(12) United States Patent
Marshel

(10) Patent No.: US 6,267,115 B1
(45) Date of Patent: Jul. 31, 2001

(54) INTRAVENOUS PROTECTING DEVICE

(76) Inventor: Florine Marshel, 4200 Pinefield Ct., Suite B, Foxridge, MD (US) 21133

( * ) Notice: Subject to any disclaimer, the term of this patent is extended or adjusted under 35 U.S.C. 154(b) by 0 days.

(21) Appl. No.: 09/668,729

(22) Filed: Sep. 25, 2000

(51) Int. Cl.$^7$ ............................................. A61F 5/37
(52) U.S. Cl. ............................. 128/877; 128/DIG. 6; 128/DIG. 26; 604/179; 604/180
(58) Field of Search ............................. 128/846, 869, 128/877, 878, DIG. 26, 879, DIG. 6, 888; 604/179, 180

(56) References Cited

U.S. PATENT DOCUMENTS

| | | | |
|---|---|---|---|
| 3,722,508 | * | 3/1973 | Roberts .................................. 128/888 |
| 3,918,446 | * | 11/1975 | Buttaravoli ............................ 604/180 |
| 4,917,112 | * | 4/1990 | Kalt ....................................... 128/888 |
| 4,941,882 | * | 7/1990 | Ward ...................................... 604/180 |
| 5,063,919 | | 11/1991 | Silverberg . |
| 5,188,608 | * | 2/1993 | Fritts ...................................... 604/179 |
| 5,415,642 | | 5/1995 | Shepherd . |
| 5,592,953 | | 1/1997 | Delao . |
| 5,643,183 | | 7/1997 | Hill . |
| 5,720,713 | | 2/1998 | Hutchison . |

\* cited by examiner

Primary Examiner—Michael A. Brown
(74) Attorney, Agent, or Firm—Venable; Richard D. Schmidt

(57) ABSTRACT

The protective device of the present invention used for an intravenous (IV) site during intravenous infusion includes a waterproof flexible wrap that wraps around a portion of a limb where an intravenous catheter enters a vein. The wrap secures the intravenous tube connected to the catheter into position and excludes water and other contaminants from the IV site allowing the patient to bathe.

14 Claims, 3 Drawing Sheets

INTRAVENOUS PROTECTING DEVICE

FIELD OF THE INVENTION

The present invention relates to protective device for a portion of a limb. Further, the present invention relates to protective device for maintaining a clean area around a portion of a limb and preventing water and other contaminants from reaching the clean area. In particular, the present invention provides a device for protecting an intravenous site of a patient from water and other contaminants during intravenous infusion and water immersion of the limb.

Intravenous ("IV") infusion is an effective route for quick administration of water, electrolytes, medications, and nutrients for a patient. The fluid directly passes through a tube connected to a catheter, then enters into the extracellular fluid in the vein. The veins in and around the cubital fossa are commonly used for venipuncture; other veins include those in the forearm and the radial area of the wrist and the hand, femoral and saphenous veins in the thigh, the foot veins, and scalp veins in infants and in the aged. An insertion of a catheter through a slit in the vein is used when veins are hard to find and long-term fluid therapy is anticipated.

The IV site must be kept dry and free from contaminants. When a patient has to bathe during IV infusion, he has to position himself to avoid contact of the affected area with water and other contaminants, and is generally limited to incomplete sponge baths causing great inconvenience and awkwardness. Patients have even tried to wrap the area with plastic tape or trash bag to prevent water intrusion. This practice is time-consuming, and the effect is unsatisfactory. Worse, the patient may have the wound or site contaminated and subject to infection.

BACKGROUND

Devices are known in the art for protecting a limb. However, no device has been invented for effective protection of a patient's intravenous site against water and other contaminants during intravenous infusion. Further, no protective device has been invented for an intravenous site which also allows the free movement of the affected limb so that the patient can help himself in the absence of a nurse.

Most of protective devices known in the art use a waterproof sleeve sealed at one end and opened at the other end for placement over a leg or an arm to protect the leg or the arm from contacting with water or other contaminants. The protective devices known in the art use elastic band and/or straps to secure the opening end of the protective sleeve onto the limb. However, the elastic band and straps are usually not tight enough to secure the entire protective sleeve onto the limb due to the huge volume of the sleeve. Very often there are openings between the protective sleeve and the limb, through which water and other contaminants leak into the sleeve. Moreover, such a protective sleeve is not flexible enough for a person's needs. The hand or foot is entirely covered in the protective sleeve and therefore unavailable for use. Such a device is inconvenient and unnecessary for the person wearing it.

Further, the protective devices of the prior art do not effectively prevent water and other contaminants from contacting an intravenous site when the person undergoing intravenous infusion must bathe. An intravenous site is where a catheter enters a vein for intravenous infusion; at the same time, the catheter is connected to a tube which is in turn connected to a liquid reservoir. During the intravenous infusion, if the patient desires to take a shower, or soak in water, or simply be outdoors during wet weather, the intravenous site is not well protected against water and contaminants. Leakage occurs at the site through the tube connecting to the catheter which enters the vein.

U.S. Pat. No. 5,720,713 teaches a protective sleeve for an intravenous site. The tube connected to the catheter enters the sleeve through a passage in a water impermeable flexible band inside the sleeve. The tube is localized by a flap and a seal. A strap secures the sleeve to the limb by wrapping around it. The protective sleeve has disadvantages. For instance, the sleeve covers the entire distal end of the limb, which is inconvenient and unnecessary. The entire sleeve solely depends on the strap to prevent it from sliding, and can easily become loose or dislocated because of the huge volume of the sleeve. In addition, there may not be enough security for the tube passing the band by the seal and flap. Additionally, this type of device is not very flexible since there is only one localized passage for the tube through the band.

U.S. Pat. No. 5,415,642 teaches a protective shield for protecting an indwelling percutaneous catheter. However, the shield is not designed for use during IV infusion and there is no tube passage through the entire structure. Besides, an adhesive is used to adhere the shield onto the skin. The structure makes it impossible for any fluid passing through a tube and a catheter at the same time.

U.S. Pat. No. 5,592,953 teaches protective sleeves for a medicinal site which are open at both ends. The sleeves are sealed with adjustable elastic sections with elastic drawstrings which circumscribe a cushioning resilient layer. There are no passages for a tube connected to a catheter for IV infusion.

U.S. Pat. No. 5,643,183 teaches a waterproof cover made of transparent polyethylene for a limb. The cover does not allow for passage of a tube; it is hermetically sealed at the distal end. The cover uses a hook and loop fastener to affixing the cover on the extremity through the folding and gathering of the sleeve, which is not effective for waterproof purposes at the proximate end.

U.S. Pat. No. 5,063,919 teaches a waterproof member which protects casts, splints, or other appliances or surgical dressings from water damage. The waterproof member uses a combination of a securing member and straps to secure the member and provides a waterproof seal between the waterproof member and the wearer. However, the waterproof member does not concern protection of an IV site; there is no passage for the tube; and the member is sealed at one end.

BRIEF SUMMARY OF THE INVENTION

The present invention provides a method and a protective device for protecting a portion of a limb against water and other contaminants when a person wearing the device takes a shower, soaks in a whirlpool or swims, participates in hydrotherapy, or is outdoors during wet weather. More particularly, the present invention is directed to a method and protective device for protecting an intravenous (IV) site having a tube connected thereto during intravenous infusion.

The protective method and device of the present invention includes providing a waterproof flexible covering or wrap that wraps one or more times around a portion of a limb where an intravenous site and a catheter entering a vein are located. A tube that connects to the catheter passes through a portion of the device covering the site by way of an opening or slit in the wrap. The tube may be secured at the innermost position of the opening by a flexible flap or by a closure of the opening. Once the tube is secured, the tube is further confined to the surface of the wrap by a second flap located on the outer surface of the first layer of the wrap. The wrap is then wrapped around the portion of the limb to cover the first layer of the wrap where the tube passes through and is secured. The inner surface of the second layer of the wrap is tightly and removably adhered or secured to the outer surface of the first layer of the wrap by an attaching or adhering means such as Velcro closure stripes or adhesives positioned on one or both surfaces. These adhering or securing portions may be positioned along the outer edges of said inner and outer surfaces.

The present invention comprises a method of protecting an intravenous catheter and infusion site from water and other contaminants by providing a water proof protective wrap having a through slit from one edge of the width of said wrap said slit intersecting an opening in an interior portion of said wrap and traversing the thickness of said wrap wherein said opening is sized to accept an intravenous tube therethrough. The water proof protective wrap is positioned over the infusion site and catheter on the limb of an individual undergoing intravenous infusion and around the intravenous tubing connected to said catheter by parting the two sides of said slit and centering said tubing in said opening. The tubing is secured to the wrap, preferably by a tab or strip that will adhere to the surface of the wrap. The length of the wrap is then wrapped around the limb until the intravenous site and tubing is covered at least once by the wrap. Thereafter the overlaying wrap portion is removably secured to an underlying portion of the wrap to retain the wrap in place.

In another aspect of the invention a device is provided for protecting an intravenous site and catheter during intravenous infusion. This device comprises a water proof protective flexible wrap wherein the wrap comprises an inner surface, an outer surface, a width and a length. The inner surface contains a sterile portion for placement over the situs of the intravenous infusion and the length is sufficient to wrap around the limb of an individual receiving the intravenous infusion and overlap the intravenous site at least once. The width is sufficient to cover the area adjacent the intravenous site to a degree sufficient to preclude water from entering the intravenous site from the side of said wrap when said wrap is secured during use. The wrap also contains a slit through both said inner and outer surfaces and traversing from one edge of said width and intersecting with an opening within the bounds of the sterile portion of the inner surface. This opening is of sufficient dimensions to allow an intravenous tube connected to the catheter to pass through the opening. An intravenous tube retainer is also positioned on an outer surface of the wrap. Preferably the wrap also includes one or more portions thereon to allow for removably securing the wrap in position once it has been wrapped around and over the intravenous site and catheter.

The present invention has advantages of protecting an IV site from water and other contaminants while allowing a person to wear it to attend various activities during intravenous infusion. The present invention has an additional benefit of allowing the limb to move freely during intravenous infusion while effectively protecting the IV site. The present invention is also useful for protecting wounded area from airborne pollutants.

DETAILED DESCRIPTION OF THE INVENTION

Figure 1:
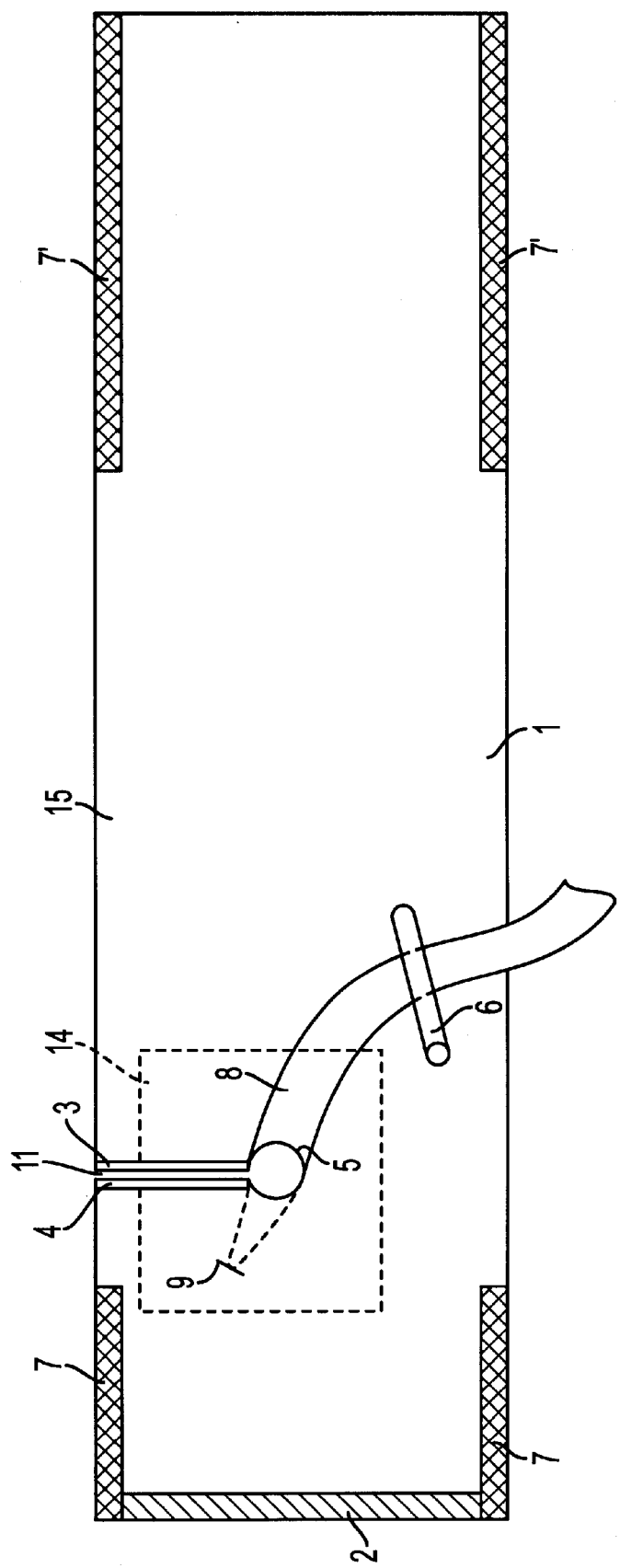
FIG. 1 shows one embodiment of the protective device of the present invention.
Figure 2:
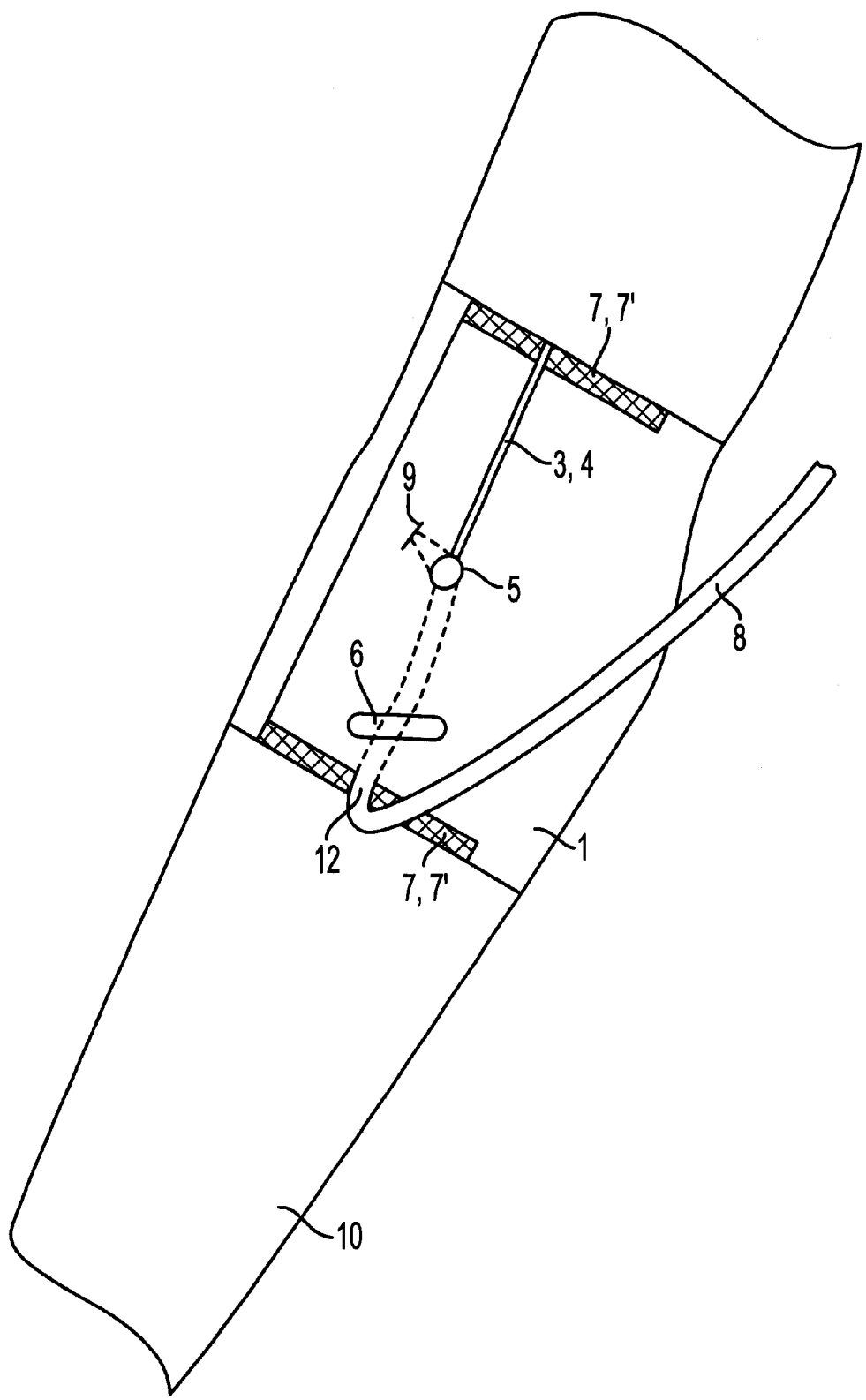
FIG. 2 shows a perspective view of the protective device of the present invention in use.

Referring to FIGS. 1 and 2, the intravenous protector wrap of the present invention is a flat piece of the wrap 1 with its length much longer than its width. The width of the the wrap must be sufficient to provide enough protection for the site on either side of the intravenous site, preferably around 4 inches for use on a limb. The wrap fits over an intravenous site 9 on a limb 10 and wraps around the portion of the limb 10 to form a cylindrical-shaped protective sleeve guard. The wrap completely covers the intravenous entry site 9 and directly prevents water, moisture, and other contaminants from contacting or invading the intravenous site 9. It is contemplated, however, that the protective wrap can be provided and sized in differing sizes, or be adjustable, to fit different individuals such as adults, children and infants.

For convenience of use it is contemplated that there is a releasable adhesive 2 or other retainer preferably provided near one end of the inner surface of the wrap 1 for initial retaining or attachment to the skin area away from the immediate IV site 9 to be protected to retain the wrap in place. In a preferred embodiment the releasable adhesive 2 is protected by a layer of non-stick film attached thereon to isolate the adhesive prior to use. After the film is removed, the adhesive 2 is exposed and used to retain the wrap to the skin area away from the site 9 to be protected. Thus, the adhesive 2 adhering to the skin serves as a fixed point for the entire wrap 1. Other types of retainers for immobilizing the wrap to a fixed position on the patient's skin can also be used. Additionally, strips of adhesive tape or can be used to retain the wrap in position. Location and positioning of the retainer is not necessary or critical to the invention.

At the IV site 9, a catheter (not shown) enters a vein. The catheter is connected to a tube 8 which is in turn connected to a liquid reservoir (not shown). In use, the sterile portion 14 on the inner layer, or the layer of the wrap that is in contact with the skin, is positioned over the IV site 9. The tube 8 then passes through both the inner layer and outer layer 15 of the wrap through an incision or slit 11 in the wrap 1. As shown in FIG. 1, the slit 11 starts from one edge of the width of the wrap, goes though both inner and outer surfaces or layers and traverses into an opening 5 which is sized to allow for the passage of the tube 8 therethrough. In each side 3 and 4 of the slit 11 is separated and placed under the catheter so that the tube passes through the opening 5. The portion 14 of the wrap 1 around the slit 11 generally does not have adhesive properties for adhering to skin and is sterile. The tube 8 is retained at the opening 5 by the closure of the slit 11 itself. The slit 11 may be merely closed under the tube 8 or it can be sealed by ridges or grooves on a portion of each side 3 and 4 of the slit 11, or each side 3 and 4 can be self-adhering.

Figure 3:
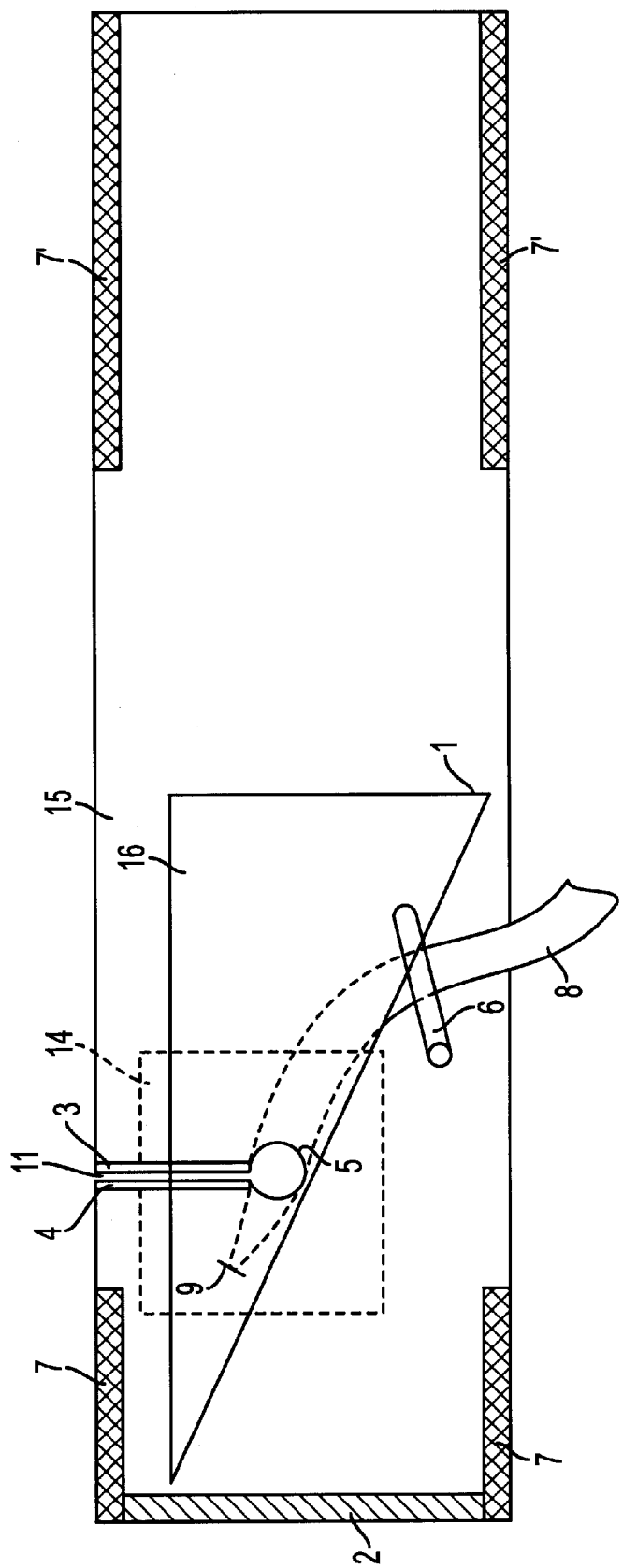
FIG. 3 shows another embodiment of the protective device of the present invention

Preferably the tube 8 is secured in the opening 5 after the closure of the slit 11, by a flexible tab 6, or some other additional flap of material adhering or otherwise attached to the outer surface 15 of the wrap 1. The tab or flap 6 not only localizes the tube 8, but will also capture or prevent water from travelling down the outside of tube 8 to contact and contaminate the IV site 9. An additional flap 16, FIG. 3, may also be attached to the outer surface 15 of wrap 1 to overlay the tube 8 to provide additional protection and possibly absorptive capacity to prevent water from traversing the outside of the tubing material and contaminating the IV site 9. Flap 16 can also be used to retain the tube into position for wrapping such as, for example, an adhesive strip or hook and loop strips to attach the free ends to the outer surface thereby retaining the tube therebetween. The flap could also contain a tube retaining means thereon or be made of material that will have self-adhering properties to retain the tube.

Once the tube 8 has been retained into position the wrap 1 is wrapped around the portion of the limb 10 to cover the IV site 9 and first wrapped layer of the wrap1 where the tube 8 is secured. The inner surface of the second layer of the wrap is tightly adhered to the outer surface 15 of the first layer of the wrap, preferably by a closure seal 7 and 7'. The seal should be waterproof and not peel away from itself when contacted with water. The seal 7 and 7' may also be selected to facilitate the removal of the wrap 1. Alternatively the wrap can be retained in position by adhesive tape or other retaining means.

Preferably the closure seals 7 and 7' are hook and loop closure strips such as that sold under the trade name Velcro or patches of adhesive material, positioned on the outer surface of the first layer and the inner surface of the second layer along their seams. Adhesive tape or other securing methods may also be employed to retain the end 2 of the wrap 1 into position.

When in use the tube 8 passes between the first layer and the second layer of the wrapped wrap 1. The tube 8 may also pass through a grooved passage (not shown) can be a disjoined area 12 along the closure means 7 and 7'. It is important that the tube 8 be carefully placed between the two layers of wrap 1 so that there is neither leakage along nor kinking or pressure compression of the tube 8 occurs during IV infusion.

The flap or other retaining means 16 used to overlay the tube and the opening 5 or the second strap 6 used to secure the tube 8 to the outer surface 15 of the first layer of the wrap 1 can also use hook and loop securing tabs in preferred embodiments. Alternatively, the flaps can be other securing means such as releasable adhering stripes. The slit 11 can also be closed through either a loop and hook fastener or other adhering means located on one or both sides 3 and 4 of the slit 11. The retainers 7 and 7' of the unit can also include hook and loop securing strips that would connect together once the wrap 1 is wrapped around the limb.

When the wrap of the present invention is used to wrap around the neck, it is important not to put too much pressure on the site. When the wrap of the present invention is used for covering a wound, the wounded area must be carefully cleaned to be free of dirt and contaminants before being covered.

The wrap of the present invention is preferably made of one or more plastic materials that are lightweight, flexible, and waterproof at least on one side or surface the of. it is also preferable that the materials used for the patient contact surfaces be hypoallergenic. Preferably, the material of the wrap is transparent or translucent so that the underlying IV site can be monitored for leakage during IV infusion. It is preferable to maintain visibility under the wrap so that the IV site can be constantly inspected for leakage. There may also be soft, preferably sterile, pad attached to the inner surface of the wrap 14 for patients' comfort. However, if the pad is made of cotton or other material that absorbs moisture it is preferred that there is no pad attached underneath the wrap unless it is place sufficient inward of the edge to prevent water seepage and contamination within the pad.

For example, the material for the wrap can be a latex, a transparent polymeric plastic material such as polyethylene, or the like. For another example, the material can be a non-latex clear plastic material for patients who are allergic to latex. The material can be so flexible that it stretches under tension such as Teflon®. Such material offers flexibility and warmth while allowing the area to "breathe" during the use.

The finished product should be packaged in a sterile package with any adhesive surfaces protected by a cover or a film which can be removed later to expose the adhesive surface. The wrap can be made in various sizes to fit adults and children. It may be produced in reusable and disposable versions, and in assortment of colors and designs. The dyes for embodying designs must be only on the outer layer of the wrap and never have to contact with the site to be protected.

In addition to provide waterproof protection for an intravenous site, the protecting device is useful for covering, including but not limited to, casts, surgical sites, bandages, sutures, burns, and the like. The protective device of the present invention effectively keeps the area dry and clean while a patient bathes, soaks in a whirlpool, participates in hydrotherapy, or goes outdoors during inclement weather. The protective device protects the site against moisture, dirt, and contaminants, thus reduces opportunity for medical complication, skin irritation, and infection. The protective device is convenient, affordable, effective, and comfortable.

What is claimed is:

1. A device for protecting an intravenous site and catheter during intravenous infusion comprising a water proof protective flexible wrap wherein said wrap comprises an inner surface, an outer surface, a width and a length wherein said inner surface contains a sterile portion for placement over the situs of the intravenous infusion and wherein the length is sufficient to wrap around the limb of an individual receiving the intravenous infusion and overlap said intravenous site at least once and wherein the width is sufficient to cover the area adjacent the intravenous site to a degree sufficient to preclude water from entering the intravenous site from the side of said wrap when said wrap is in use, and wherein said wrap contains a slit through both said inner and outer surfaces from one edge of said width to an opening within the bounds of the sterile portion of the inner surface and of sufficient dimensions to allow an intravenous tube connected to said catheter to pass through said opening, said wrap further comprising a intravenous tube retainer on said outer surface.

2. The device for protecting an intravenous site and catheter during intravenous infusion of claim 1 wherein the outer surface of the water proof protective flexible wrap is constructed from a water proof material.

3. The device for protecting an intravenous site and catheter during intravenous infusion of claim 2 wherein the water proof material is hypoallergenic.

4. The device for protecting an intravenous site and catheter during intravenous infusion of claim 1 wherein the water proof protective flexible wrap is at least partially constructed from a transparent material sufficient to allow the intravenous site to be viewed during use of said wrap.

5. The device for protecting an intravenous site and catheter during intravenous infusion of claim 1 wherein the inner and outer surfaces of said wrap removably adhere to each other.

6. The device for protecting an intravenous site and catheter during intravenous infusion of claim 1 further comprising removable adhering means on the inner and outer surfaces of said wrap.

7. The device for protecting an intravenous site and catheter during intravenous infusion of claim 1 further comprising a flap attached to the outer surface and sized to overlay the slit and opening.

8. The device for protecting an intravenous site and catheter during intravenous infusion of claim 7 wherein said flap retains said tube to said outer surface.

9. A method of protecting an intravenous catheter and infusion site from water and other contaminants comprising:

provinding a water proof protective wrap having a through slit from one edge of the width of said wrap said slit intersecting an opening in an interior portion of said wrap and traversing the thickness of said wrap wherein said opening is sized to accept an intravenous tube therethrough;

placing said water proof protective wrap over the infusion site and catheter on the limb of an individual undergoing intravenous infusion and around the intravenous tubing connected to said catheter by parting the two sides of said slit and centering said tubing in said opening;

securing said tubing to said wrap;

wrapping the length of said wrap around said limb until said intravenous site and tubing is covered by said wrap; and removably securing said overlaying wrap portion to an underlying wrap portion.

10. The method of claim 9 wherein the wrap provided is constructed of hypoallergenic material.

11. The method of claim 9 wherein the securing of the underlying and overlaying portion of said wrap is accomplished by providing hook and loop closure means to at least a portion of said wrap inner and outer surfaces.

12. The method of claim 9 wherein the securing of the underlying and overlaying portion of said wrap is accomplished by providing removably adhering portions to at least a portion of at least one of said wrap inner and outer surfaces.

13. The method of claim 9 further comprising:

providing a flap attached to said outer surface; and overlaying said flap over said secured tube such that water is prevented from traversing said tube to said intravenous site.

14. The method of claim 9 further comprising:

providing a flap attached to said outer surface; and overlaying and securing said flap to said tube such that water is prevented from traversing said tube to said intravenous site.

* * * * *